(12) United States Patent
Edwards et al.

(10) Patent No.: US 8,394,094 B2
(45) Date of Patent: Mar. 12, 2013

(54) SURGICAL INSTRUMENT

(75) Inventors: Thomas R. K. Edwards, Llanishen (GB); Anthony K. Atwell, Rogerstone (GB)

(73) Assignee: Gyrus Medical Limited, Cardiff (GB)

( * ) Notice: Subject to any disclaimer, the term of this patent is extended or adjusted under 35 U.S.C. 154(b) by 738 days.

(21) Appl. No.: 12/379,676

(22) Filed: Feb. 26, 2009

(65) Prior Publication Data
US 2009/0234355 A1 Sep. 17, 2009

Related U.S. Application Data

(60) Provisional application No. 61/064,755, filed on Mar. 25, 2008.

(30) Foreign Application Priority Data

Mar. 13, 2008 (GB) .................................. 0804688.0

(51) Int. Cl.
*A61B 18/18* (2006.01)
(52) U.S. Cl. ............................................. 606/48
(58) Field of Classification Search ............... 606/206, 606/51, 48
See application file for complete search history.

(56) References Cited

U.S. PATENT DOCUMENTS

| | | | |
|---|---|---|---|
| 6,129,735 A | 10/2000 | Okada et al. | |
| 6,174,309 B1 * | 1/2001 | Wrublewski et al. | 606/45 |
| 7,033,356 B2 | 4/2006 | Latterell et al. | |
| 2001/0037109 A1 | 11/2001 | Yamauchi et al. | |
| 2004/0049185 A1 | 3/2004 | Latterell et al. | |
| 2005/0113820 A1 | 5/2005 | Goble et al. | |

FOREIGN PATENT DOCUMENTS

| | | |
|---|---|---|
| DE | 10 2004 026 179 A1 | 12/2005 |
| EP | 1 905 370 A1 | 4/2008 |
| WO | WO 99/40861 A1 | 8/1999 |
| WO | WO 2004/032777 A1 | 4/2004 |
| WO | WO 2005/072634 A2 | 8/2005 |

OTHER PUBLICATIONS

Written Opinion of the International Searching Authority dated May 11, 2009 in International Patent Application No. PCT/GB2009/000557.
International Search Report dated May 11, 2009 in International Patent Application No. PCT/GB2009/000557.
Nov. 21, 2011 European Examination Report issued in UK Application No. GB1014031.7.

* cited by examiner

*Primary Examiner* — Laura A Bouchelle
*Assistant Examiner* — Weng Lee
(74) *Attorney, Agent, or Firm* — Oliff & Berridge, PLC

(57) ABSTRACT

An end effector assembly for an electrosurgical instrument comprises a pair of opposing first and second jaw members. At least one of the jaw members is movable relative to the other between a first open position in which the jaw members are disposed in a spaced relation relative to one another, and a second closed position in which the jaw members cooperate to grasp tissue therebetween. The first jaw member comprises first and second sealing members extending along a length of the jaw and being separated by an insulating member therebetween, and is provided with an electrically-conductive cutting electrode supported on the insulting member. The second jaw member comprises third and fourth sealing members extending along the jaw and being separated by a recess therebetween, an electrically-insulating anvil being located in the recess opposite the cutting electrode. The electrically-insulating anvil is located on a support member attached to one or both of the third and fourth sealing members, and the anvil and support member are such that the anvil is spring mounted with respect to the third and fourth sealing members and such that the anvil can move within the recess by at least 0.5 mm when tissue is grasped between the jaws of the end effector assembly.

13 Claims, 5 Drawing Sheets

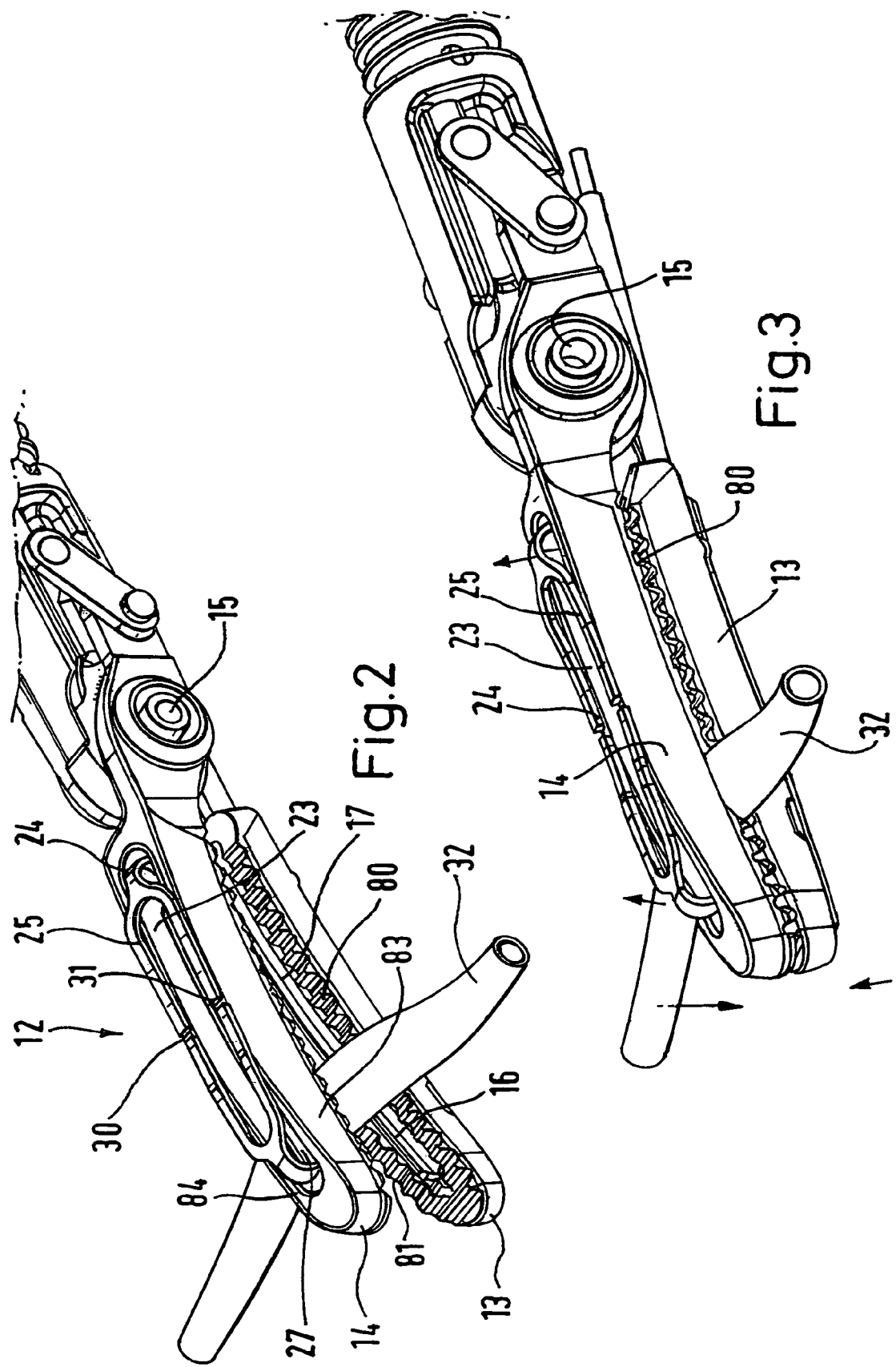

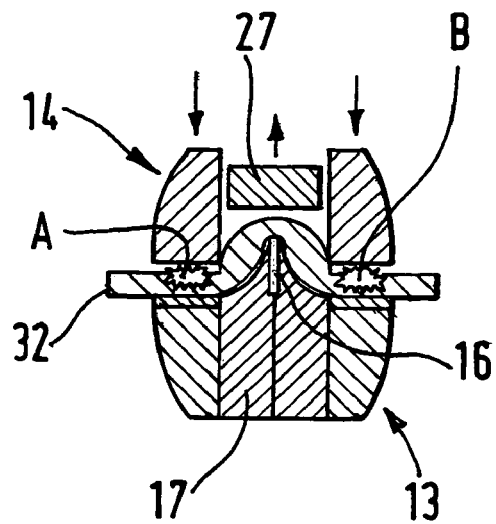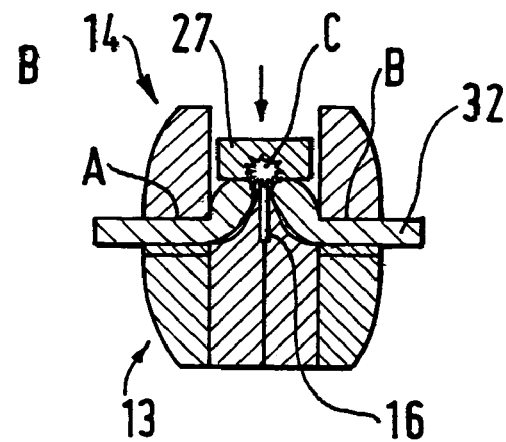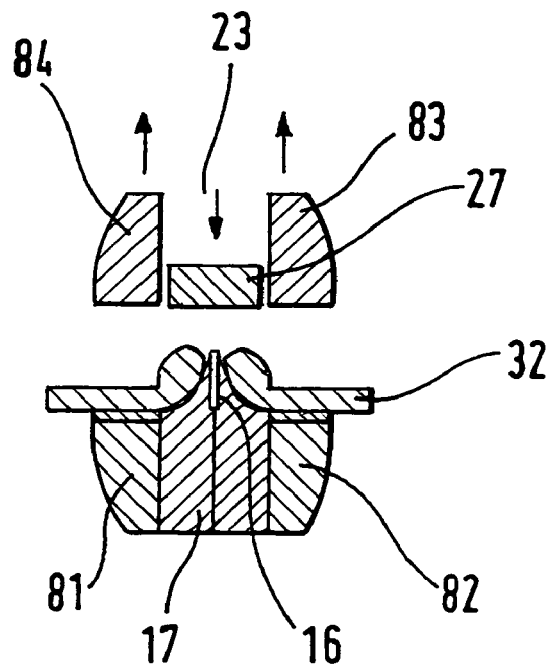

SURGICAL INSTRUMENT

CROSS-REFERENCE TO RELATED APPLICATION

This application claims the benefit of Provisional Application No. 61/064,755 filed Mar. 25, 2008, the entire contents of which are hereby incorporated by reference in this application.

FIELD OF THE INVENTION

This invention relates to an end effector for an electrosurgical instrument such as a forceps or other electrosurgical instrument for use in the treatment of tissue.

BACKGROUND OF THE INVENTION

The specification of U.S. Pat. No. 6,174,309 (Wrublewski) discloses an electrosurgical instrument in which tissue is sealed between the jaws of an end effector, before an electrosurgical signal is supplied to an electrosurgical cutting electrode in order to sever the tissue. In that instrument, the electrosurgical cutting electrode is movably biased against the tissue being severed. U.S. Pat. No. 7,033,356 relates to a more modern version of that instrument, in which tissue is tensioned across a jaw with a raised cross-section in order to assist in the severing of the tissue. The present invention provides an improvement to both of these earlier designs of instrument.

SUMMARY OF THE INVENTION

Accordingly, there is provided an end effector assembly for an electrosurgical instrument, the end effector assembly comprising a pair of opposing first and second jaw members, at least one of the jaw members being movable relative to the other between a first open position in which the jaw members are disposed in a spaced relation relative to one another, and a second closed position in which the jaw members cooperate to grasp tissue therebetween, the first jaw member comprising first and second sealing members extending along the length of that jaw member, the first and second sealing members being separated by an insulating member therebetween, and being provided with an electrically-conductive cutting electrode supported on the insulating member, and the second jaw member comprising third and fourth sealing members extending along that jaw member, the third and fourth sealing members being separated by a recess therebetween, an electrically-insulating anvil being located in the recess opposite the cutting electrode, the electrically-insulating anvil being located on a support member attached to one or both of the third and fourth sealing members, the anvil and the support member being such that the anvil is spring mounted with respect to the third and fourth sealing members such that the anvil can move within the recess by at least 0.5 mm when tissue is grasped between the jaw members.

The prior art Wrublewski patent provides one embodiment in which a "counter-anvil" is mounted on expansion or leaf springs to be biased against the tissue instead of the cutting blade. However, the present inventors have recognized that the performance of the instrument can be improved if the anvil is movable by an amount much greater than that ever contemplated in the Wrublewski patent. Accordingly, the anvil is spring mounted such that it can move by at least 0.5 mm, preferably at least 1 mm and conceivably by as much as 2.5 mm when tissue is grasped between the jaws of the end effector assembly. This significant spring loading allows for a much greater force to be exerted on the tissue between the sealing members, as compared with that exerted between the cutting electrode and the corresponding anvil, thereby permitting both effective sealing and cutting of tissue over a range of tissue thicknesses. Although the anvil is described as electrically-insulating, this does not mean that the whole of the anvil is necessarily made from an insulating material. While the anvil may be formed as a unitary member, it may also be formed from a non-insulating material such as metal, which is coated or covered with an electrically-insulating surface material.

The sealing members are designed to act as electrosurgical electrodes for the coagulation of tissue held between the jaws. Accordingly, the first and second sealing members are conveniently adapted to be connected to a source of electrosurgical energy such that they form a first electrode for conducting electrosurgical energy through tissue held between the jaw members. Similarly, the third and fourth sealing members are conveniently adapted to be connected to the source of electrosurgical energy such that they form a second electrode for conducting electrosurgical energy through tissue held between the jaw members. Therefore, the sealing members of each jaw member are commonly connected to form a single electrode on each jaw member. Although this arrangement is perfectly sufficient to coagulate tissue placed between the jaw members, those skilled in the art will be aware of alternative constructions that are known and used. These include arrangements in which the first and second sealing members are not commonly connected, but have an insulator therebetween, as well as an insulator separating them from the cutting electrode. In this way, the first and second sealing members can be independently connected to different poles of an electrosurgical generator. A similar arrangement can be applied to the third and fourth sealing members on the other jaw member of the end effector. These variations can be applied without departing from the intended scope of the present invention.

According to one convenient arrangement, the spring mounting of the anvil is achieved by making it spring mounted with respect to the support member. Alternatively, the spring mounting of the anvil can be achieved by making the support member spring mounted with respect to the third and fourth sealing members. Whichever method of spring mounting is employed, the anvil must be mounted so that a significant degree of movement is permitted with respect to the sealing members.

To allow even more movement of the anvil, the recess preferably passes completely through the third and fourth sealing members. In this way, one or both of the support member and the anvil can protrude out of the recess away from the cutting electrode when tissue is grasped between the jaw members of the end effector assembly. This construction allows for more movement of the anvil than would be possible with other, more enclosed constructions.

The end effector assembly of the present invention should also be considered in combination with an actuation mechanism for moving the jaw members between the first open position and the second closed position. Preferably, the actuation mechanism is adapted to apply a pressure of between 0.5 and 1.0 M Pa to tissue grasped between the sealing members. Additionally, the actuation mechanism and the spring mounted anvil is adapted to apply a force of between 0.08 and 0.25 N/mm to tissue grasped between the anvil and the cutting electrode. However, these figures are presented as guidelines only, as the pressure applied to the tissue will vary depending upon several factors, including the shape and size of the jaw members, and the shape, size and consistency of the tissue grasped between the jaw members.

Similarly, the actuation mechanism and the spring mounted anvil are preferably such that the ratio of the force applied to tissue grasped between the sealing members as compared to that applied between the anvil and the cutting electrode is conveniently between 8:1 and 4:1, preferably between 7:1 and 5:1, and typically approximately 6:1.

Preferably, the actuation mechanism is constituted by a scissors-type handle assembly.

BRIEF DESCRIPTION OF THE DRAWINGS

The invention will now be described in more detail, by way of example, with reference to the drawings, in which:

FIG. 2 is a perspective view of the end effector assembly of the instrument of FIG. 1, shown with the jaws in the open position;

FIG. 3 is a perspective view of the end effector assembly of the instrument of FIG. 1, shown with the jaws in the closed position;

FIGS. 4 to 9 are schematic sectional diagrams of the end effector assembly of the instrument of FIG. 1, in different stages of operation;

DESCRIPTION OF PREFERRED EMBODIMENTS

Figure 1:
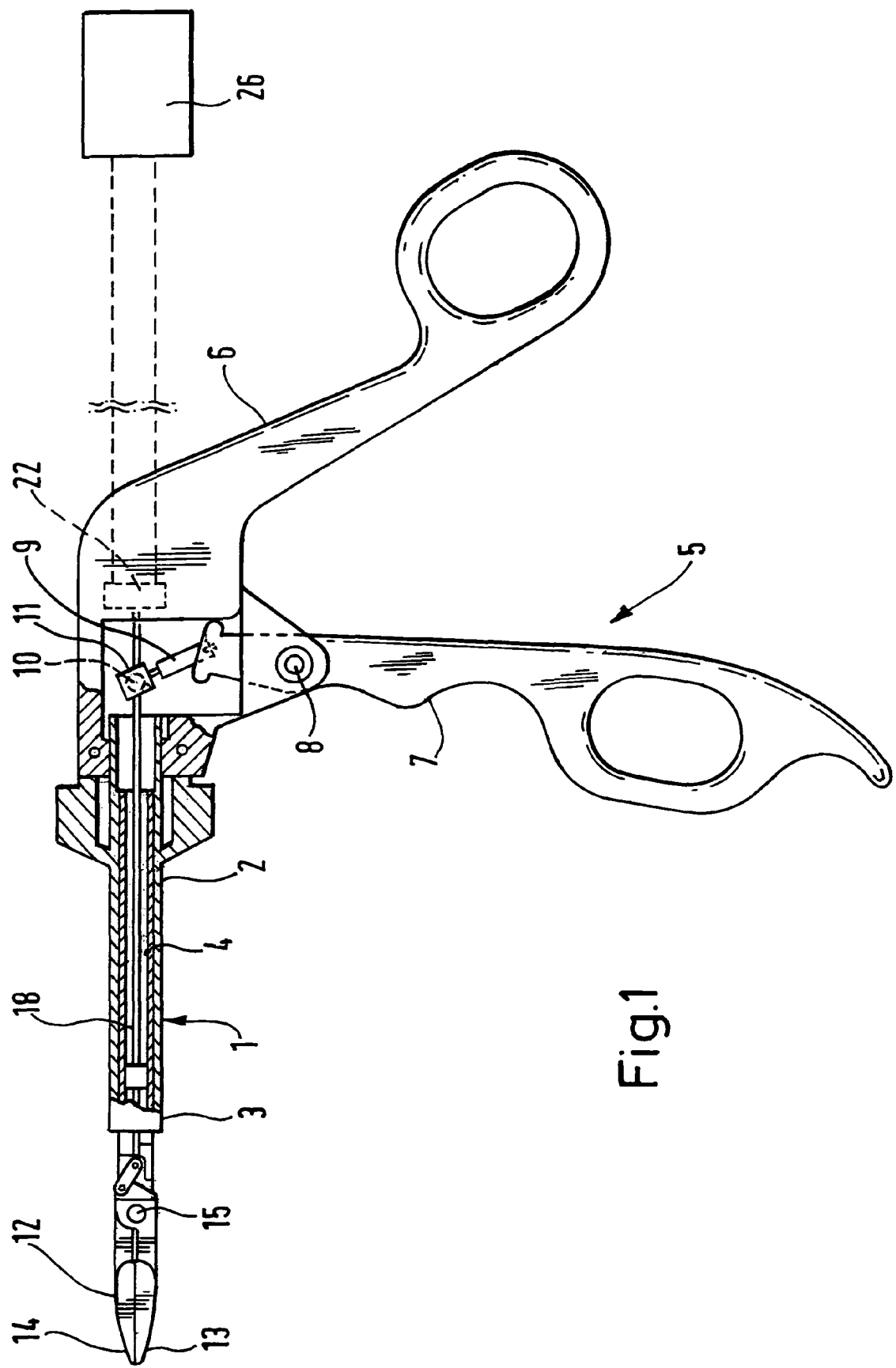
FIG. 1 is a schematic sectional view of a surgical instrument including an end effector assembly constructed in accordance with the invention.

Referring to FIG. 1, a bipolar forceps device includes an elongate tubular member 1 with a proximal end 2, a distal end 3, and a lumen 4 which extends for the entire length of the tubular member. An actuation mechanism is provided at the proximal end 2 of the tubular member 1, the actuation mechanism being constituted by a scissors-type handle assembly 5 with a first handle 6 and a second handle 7. The second handle 7 is pivotable with respect to the first handle 6, about a pivot pin 8. In a known design of actuation mechanism, the second handle 7 has a pin 9 affixed to the top thereof, such that movement of that handle causes a corresponding movement of a sphere 10 supported in a U-shaped cradle 11.

Fitted into the distal end 3 of the tubular member 1 is a forceps jaw assembly 12, more particularly shown in FIG. 2. The jaw assembly 12 comprises a first jaw member 13 and a second jaw member 14, pivotally joined to each other by an insulated rivet 15. The jaw member 13 is constituted by two tissue-contacting members 80 and 81, separated by an insulator 17, typically made of ceramic or other insulating material. The tissue-contacting members 80 and 81 constitute sealing members for sealing against tissue gripped by the jaw member 13. The jaw member 13 is also provided with a relatively-long, but narrow cutting electrode 16 mounted on the insulator 17. The jaw members 13 and 14, together with the cutting electrode 16, are connected to an electrosurgical generator 26 by means of a connector 22, and wires or conductive rods 18 running through the lumen 4 of the tubular member 1.

As shown in FIG. 2, the cutting electrode 16 is in the form of an elongate rail, extending along the length of the jaw member 13. The rail 16 is mounted on top of the ceramic insulator 17, such that it is insulated from the tissue-contacting members 80 and 81 of the conductive jaw member 13. The rail 16 is typically 100 to 200 microns in width, and protrudes from the ceramic insulator 17 by a distance of approximately 50 microns. When the jaw assembly 12 is in its closed position, the rail 16 is received in a corresponding longitudinal recess 23 in the jaw member 14, as will now be described in further detail.

The recess 23 runs completely through the jaw member 14 from top to bottom, creating an opening therein. This recess divides the jaw member 14 into two further tissue-contacting members 83 and 84. The tissue-contacting members 83 and 84 constitute sealing members for sealing against tissue gripped by the jaw member 14. A support member 24 is received within the recess 23, the support member being in the form of a sprung frame 25, and being attached to the top of the jaw member 14 by welding at positions 30 and 31. A longitudinally-extending anvil 27 depends from the frame 25, the anvil 27 being formed of an insulating polymer material, and being aligned with the cutting electrode 16 in the jaw member 13. When the jaw members 13 and 14 are closed, as shown in FIG. 3, the anvil 27 pushes the tissue 32 against the cutting electrode 16. The anvil 27 is spring mounted by the support member 24 such that it can move by at least 0.5 mm, preferably by at least 1 mm, and conceivably by as much as 2.5 mm when tissue is grasped between the two jaw members 13 and 14.

Figure 4:
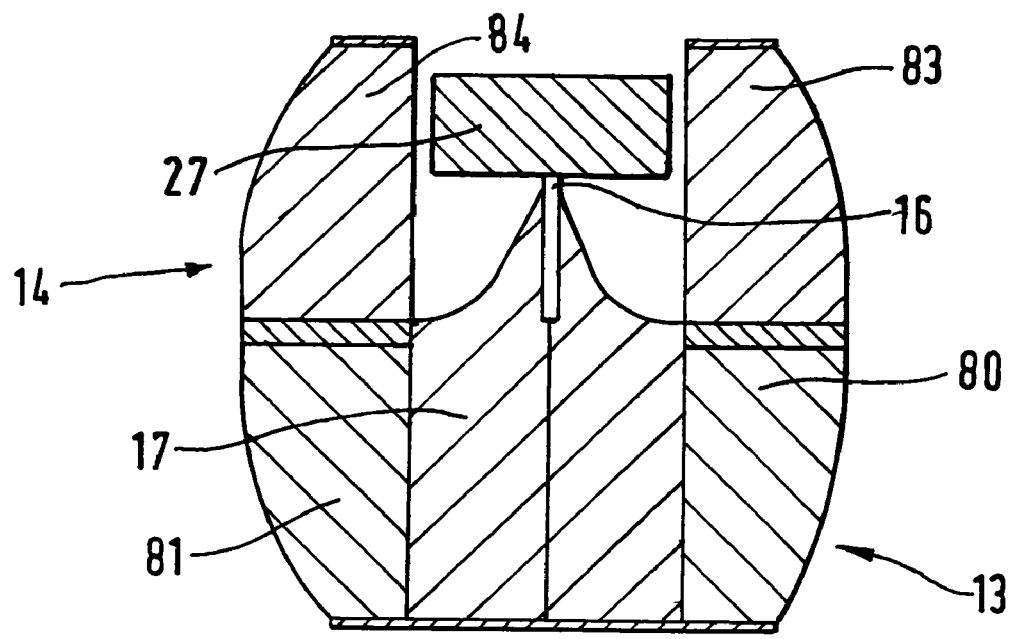

The operation of the cutting forceps instrument will now be described, with reference to FIGS. 4 to 9, which are schematic diagrams showing the simplified movement of the various key components. FIG. 4 shows the jaw members 13 and 14 in their rest position, closed but with no tissue grasped therebetween. The cutting electrode 16 pushes the anvil 27 upwardly against the support member 24 (not shown in FIGS. 4 to 9).

Figure 5:
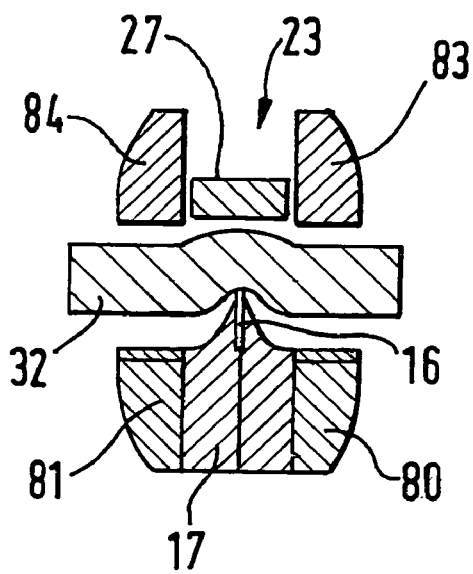
Figure 6:
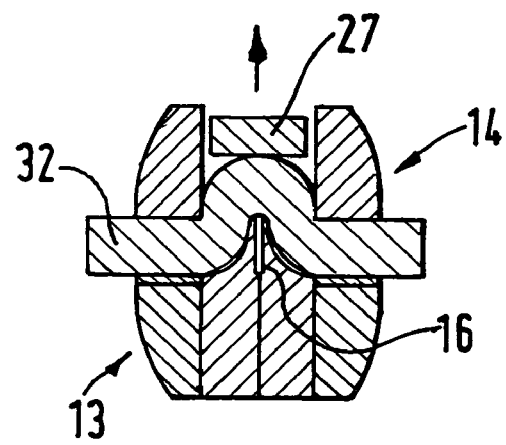
Figure 10:
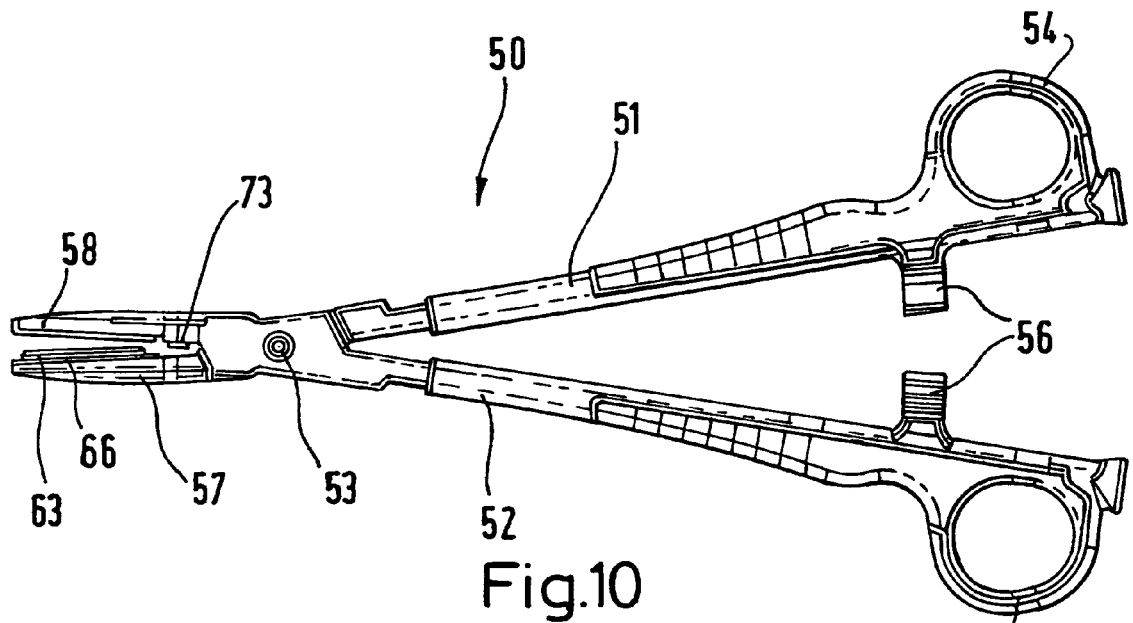
FIG. 10 is a side view of an alternative embodiment of surgical instrument including an end effector assembly constructed in accordance with the invention.

FIG. 5 shows the jaw members 13 and 14 in their open position, with the tissue 32 therebetween. With the jaw members 13 and 14 in the open position, the anvil 27 is no longer pushed upwardly by the cutting electrode 16, and consequently assumes a position more level with the base of the jaw member 14. The jaw members 13 and 14 are then closed as shown in FIGS. 6 and 7, such that the tissue 32 is squeezed between the jaw members. The anvil 27 is pushed upwardly by the tissue 32 against the spring action of the support member 24, so as not to exert so great a force on the tissue as to squeeze the tissue against the cutting electrode 16 as is supplied between the tissue-contacting members 83 and 84 of the jaw members 13 and 14. Typically, the pressure exerted on the tissue 32 by the tissue-contacting members 80, 81, 83 and 84 of the jaw members 13 and 14 in the sealing areas A and B as depicted in FIG. 7 is between 0.5 and 1.0 M Pa.

When the jaw members 13 and 14 have been fully closed, the electrosurgical generator 26 is actuated to supply a coagulating RF signal between the jaw members. This coagulates the tissue 32 in the sealing areas A and B and the tissue may shrink in size due to this coagulating action. After several seconds, the tissue 32 in the sealing areas A and B has been coagulated and the coagulating RF signal is discontinued, and replaced by a cutting RF signal supplied between the cutting electrode 16 and the jaw members 13 and 14. This is shown in FIG. 8, during which time the spring movement of the anvil 27 exerts a force against the tissue 32 of typically between 0.08 and 0.25 N/mm. The cutting electrode 16 electrosurgically severs the tissue 32 in the cutting area C as shown in FIG. 8, the cutting area C lying between the sealing areas A and B such that blood flow to the cutting area is prevented. The jaw members 13 and 14 can then be re-opened as shown in FIG. 9 to release the severed tissue 32.

The spring-loading of the anvil 27 allows for a differential force to be applied to the tissue 32 at the sealing areas A and B as compared to the cutting area C. This allows for a sufficient force to be applied to the sealing areas A and B to ensure effective sealing, without the same force being applied between the anvil 27 and the cutting electrode 16. Thus, there is much less likelihood of problems being encountered where the force exerted between the anvil 27 and the cutting electrode 16 is sufficient to cause a mechanical cutting of the tissue 32 before the electrosurgical cutting signal is supplied to the tissue. In addition, the spring loading of the anvil 27 allows the device to adapt to tissue shrinkage caused by the coagulation of the tissue. If shrinkage occurs, the spring-loaded anvil 27 ensures that a controlled force is still applied against the cutting electrode 16.

Although the forceps device of FIGS. 1 to 9 is shown as an endoscopic instrument, the invention can also be employed in connection with an open instrument 50, as will be described with reference to FIGS. 10 to 13. The instrument 50 comprises two longitudinal members 51 and 52, mounted for pivotal movement by means of a pivot pin 53. The proximal end of the member 51 is in the form of a handle portion 54, and the proximal end of the member 52 is in the form of a handle portion 55. A ratchet mechanism 56 is provided on each handle portion 54, 55 for locking the handle portions when they are moved together into their closed position.

Distal of the pivot pin 53, the longitudinal member 51 forms a jaw member 57, while the longitudinal member 52 forms a jaw member 58. Movement of the handle portions 54 and 55 causes the jaw members 57 and 58 to open and close.

Figure 11:
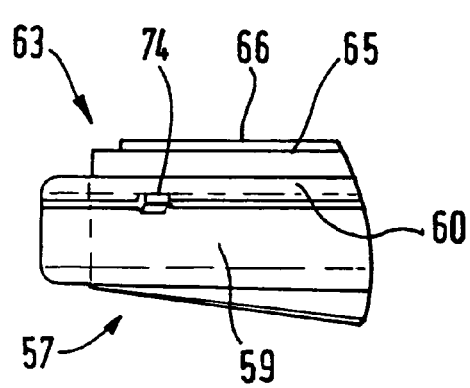
FIG. 11 is an enlarged schematic side view of a part of the end effector assembly of the instrument of FIG. 10.
Figure 12:
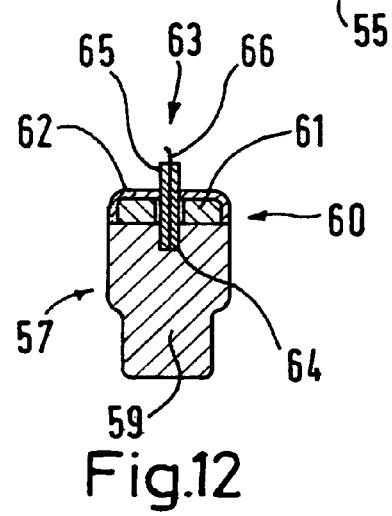
FIG. 12 is an enlarged sectional view of a part of the end effector of FIG. 11.
Figure 13:
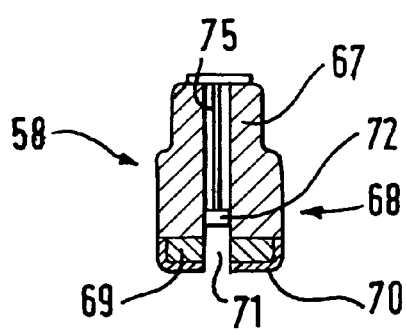
FIG. 13 is an enlarged sectional view of a different part of the end effector of FIG. 11.

With reference to FIGS. 11 and 12, the jaw member 57 comprises an integral base portion 59 on which is mounted a shim member 60, secured by means of clips 74. The shim member 60 comprises an insulating strip 61 covered by a metallic surface electrode 62. A cutting electrode assembly 63 is mounted in a recess 64 running longitudinally along the jaw member 57. The cutting electrode assembly 63 comprises a raised insulator block 65, typically made of a ceramic material, and a cutting electrode 66 mounted in a further longitudinal recess in the insulator block. The cutting electrode 66 is typically 100 microns in width, and protrudes from the insulator block 65 by a distance of approx 425 microns.

The opposite jaw member 58 (shown in FIG. 13) also comprises a base portion 67 and a shim member 68. The shim member 68 also comprises an insulting strip 69 covered by a metallic surface electrode 70. The shim member 68 includes a central recess 71 in which the cutting electrode assembly 63 of the jaw member 57 can be received when the jaw members 57 and 58 are in their closed position. The recess 71 runs completely through the jaw member 58, and contains an anvil 72 supported on a resilient frame member 75 attached by welding to the top of that jaw member. A stop member 73, mounted on one of the jaw members 57, 58, regulates the separation of the jaw members when they are in their closed position.

The operation of the instrument of FIGS. 10 to 13 is essentially similar to that of the endoscopic instrument previously described, with the anvil 72 moving by up to 0.75 mm when tissue is engaged between the cutting electrode 66 and the anvil 72.

In each of the embodiments described above the actuation mechanism 5 and the spring-mounted anvil 27 are such that the ratio of the force applied to tissue grasped between the sealing members 80, 81 and 83, 84 as compared to that applied between the anvil and the cutting electrode is between 8:1 and 4:1, and preferably between 7:1 and 5:1, and more preferably that ratio is approximately 6:1.

This invention has been described herein in considerable detail in order to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention. In addition to different constructions of the instrument, different types of RF coagulating or RF cutting signals, or even a blend of both coagulating and cutting signals can be supplied to the electrodes. Our published US patent application US 2005/0113820 describes one type of blended signal that is particularly effective with this type of coagulating and cutting procedure.

What is claimed is:

1. An end effector assembly for an electrosurgical instrument, the end effector assembly comprising:

a pair of opposing first and second jaw members, at least one of the jaw members being movable relative to the other between a first open position in which the jaw members are disposed in a spaced relation relative to one another, and a second closed position in which the jaw members cooperate to grasp tissue therebetween, wherein:

the first jaw member comprising first and second sealing members extending along a length of that jaw member, the first and second sealing members being separated by an insulating member therebetween, and being provided with an electrically-conductive cutting electrode supported on the insulating member, the second jaw member comprising third and fourth sealing members extending along that jaw member, the third and fourth sealing members being separated by a recess therebetween, an electrically-insulating anvil being located in the recess opposite the cutting electrode, the electrically-insulating anvil being located on a support member attached to one or both of the third and fourth sealing members, the anvil and the support member being such that the anvil is spring mounted with respect to the third and fourth sealing members such that the anvil can move within the recess by greater than 1 mm when tissue is grasped between the jaw members, the recess passes completely through the third and fourth sealing members, and one or both of the support member and the anvil can protrude out of the recess away from the cutting electrode when the tissue is grasped between the jaw members.

2. An end effector assembly according to claim 1, wherein the first and second sealing members are adapted to be connected to a source of electrosurgical energy such that they form a first electrode for conducting electrosurgical energy through the tissue held between the jaw members.

3. An end effector assembly according to claim 2, wherein the third and fourth sealing members are adapted to be connected to the source of electrosurgical energy such that they form a second electrode for conducting electrosurgical energy through the tissue held between the jaw members.

4. An end effector assembly according to claim 1, wherein the anvil is spring mounted with respect to the third and fourth sealing members such that the anvil can move by at least 2.5 mm when tissue is grasped between the jaw members.

5. An end effector assembly according to claim 1, wherein the anvil is spring mounted with respect to the support member.

6. An end effector assembly according to claim 1, wherein the support member is spring mounted with respect to the third and fourth sealing members.

7. An end effector assembly according to claim 1, in combination with an actuation mechanism for moving the jaw members between the first open position and the second closed position.

8. An end effector assembly according to claim 7, wherein the actuation mechanism is adapted to apply a pressure of between 0.5 and 1.0 M Pa to tissue grasped between the sealing members.

9. An end effector assembly according to claim 7, wherein the actuation mechanism and the spring-mounted anvil are adapted to apply a force of between 0.08 and 0.25 N/mm to tissue grasped between the anvil and the cutting electrode.

10. An end effector assembly according to claim 7, wherein the actuation mechanism and the spring-mounted anvil are such that a ratio of the force applied to tissue grasped between the sealing members as compared to that applied between the anvil and the cutting electrode is between 8:1 and 4:1.

11. An end effector assembly according to claim 10, wherein the actuation mechanism and the spring-mounted anvil is such that the ratio of the force applied to tissue grasped between the sealing members as compared to that applied between the anvil and the cutting electrode is between 7:1 and 5:1.

12. An end effector assembly according to claim 10, wherein the actuation mechanism and the spring-mounted anvil is such that the ratio of the force applied to tissue grasped between the sealing members as compared to that applied between the anvil and the cutting electrode is approximately 6:1.

13. An end effector assembly according to claim 7, wherein the actuation mechanism is constituted by a scissors-type handle assembly.

* * * * *